United States Patent [19]
Botimer

[11] Patent Number: 5,738,675
[45] Date of Patent: Apr. 14, 1998

[54] LIMB CLAMP FOR SURGERY

[76] Inventor: Gary D. Botimer, 13753 Locust La., Nampa, Id. 83686

[21] Appl. No.: 746,392

[22] Filed: Nov. 8, 1996

[51] Int. Cl.⁶ ........................................ A61B 19/00
[52] U.S. Cl. ........................................ 606/1; 606/130
[58] Field of Search ........................ 602/25–36; 606/1, 606/108, 130, 151, 157, 203, 204; 269/329; D24/190, 183; 600/26, 27, 35, 36

[56] References Cited

U.S. PATENT DOCUMENTS

| | | |
|---|---|---|
| D. 285,967 | 9/1986 | Murphy . |
| 3,802,692 | 4/1974 | Lipson . |
| 3,880,417 | 4/1975 | Burris et al. . |
| 4,291,229 | 9/1981 | Patt . |
| 4,299,213 | 11/1981 | Violet . |
| 4,373,709 | 2/1983 | Whitt .................. 606/203 |
| 4,457,302 | 7/1984 | Caspari et al. . |
| 4,526,165 | 7/1985 | Mielink ................ 606/203 |
| 4,526,355 | 7/1985 | Moore et al. . |
| 4,717,133 | 1/1988 | Walsh et al. . |
| 4,766,891 | 8/1988 | Schultz . |
| 5,014,970 | 5/1991 | Osipov . |

FOREIGN PATENT DOCUMENTS 0106592  5/1917  United Kingdom .............. 606/203

*Primary Examiner*—Glenn K. Dawson
*Attorney, Agent, or Firm*—Ken J. Pedersen; Barbara S. Pedersen

[57] ABSTRACT

Embodiments of a limb clamp assembly are shown and described, each having one or more articulated arms for wrapping at least partially around a leg or other extremity, for holding the leg motionless for examination or surgery. The preferred arm or arms extend generally horizontally when open, so that the limb enters the clamp from the side. a strap means may extend around the outside of the arm or arms to further encircle the limb and to close the clamp by its being pulled tight and fastened at each of its ends to the clamp. Preferably, the clamp has one or two arms, each with a joint connecting the arm to a rigid base and a joint connecting two sections of the arm. Preferably, the clamp assembly is used by inserting the limb into the interior of the clamp, swinging a strap up around the outside of the arm or arms, tightening the strap to pull the arms around the limb, and locking the strap to the base. A cam system or gear wheel system are examples of devices for tightening and locking the strap in position.

20 Claims, 10 Drawing Sheets

LIMB CLAMP FOR SURGERY

BACKGROUND OF THE INVENTION

1. Field of the Invention

This invention relates, in general, to clamps for holding legs or other limbs during examination, treatment, or surgery. More specifically, this invention relates to a leg clamp which is secured to an operating table, and which efficiently, quickly, and predictably secures around a patient's thigh for holding the leg and knee motionless during arthroscopic surgery.

2. Related Art

In the field of orthopedic medicine, for example, clamps are frequently used to secure human extremities in a preferred position for examination and surgery. For such precise procedures as arthroscopic knee surgery, a leg clamp is needed which holds a thigh motionless during the surgery, and which preferably is adjustable to fit various limb sizes and to fill the need for various degrees of tightness around the patient's limb or around a tourniquet cuff.

In the past, the need for extremity clamps has been filled by such devices as shown in U.S. Pat. Nos. 4,766,892 (Kreitman), and 4,526,355 (Moore), 4,373,709 (Whitt), 4,252,306 (Johnson, et al.), and 4,181,297 (Nichols). These clamps feature generally vertical, rigid restraining arms, for extending up on either side of the patient's thigh, and for being moved laterally together to squeeze or contain the sides of the thigh.

Some extremity clamps have included belts or strips that buckle around the vertical arms of the clamp, or around the patient's leg or a cushion or cuff surrounding the leg. Kreitman or Murphy (U.S. Pat. No. 4,545,573) illustrate such belts or strips.

Still, there is a need for an improved system that provides quick, reproducible, accurate, and comfortable clamping of a limb to an operating or examination table. There is a need for a high quality device that may be universally used for limbs of various sizes and that is economically manufactured and maintained.

SUMMARY OF THE INVENTION

This invention comprises an extremity clamping assembly, including an articulated arm or arms for receiving or supporting a patient's limb. The arm or arms preferably extend generally in a horizontal direction from a base region of the clamp, so that the clamp opens to the side. The arm(s) preferably may be easily moved to accommodate a wide range of limb sizes, from very large to very small, to accommodate both large adults to small children.

The clamp preferably includes a strap means, such as a belt, a flexible band, a chain-link band, etc., which has a first end extending from near the articulated arm, around or partially around the patient's limb, to be secured near its other end near a second articulated arm or near the clamp base region.

Preferably, the clamp assembly includes a fastening means for the belt, which may include a cam-style tightening and locking means for tightening the strap means to the desired degree and locking it in place for the medical procedure.

The articulated arm, strap means, and tightening and locking means provide a clamp assembly that can be opened wide to easily accept a limb, quickly wrapped and secured around the limb, and easily tightened a precise and reproducible amount. Using this assembly requires a minimum of manipulation of the limb and the clamp parts. The clamp assembly has an attractive and simple outer appearance, and easily-reachable and operable adjustment mechanisms.

DESCRIPTION OF THE PREFERRED EMBODIMENTS

Figure 7:
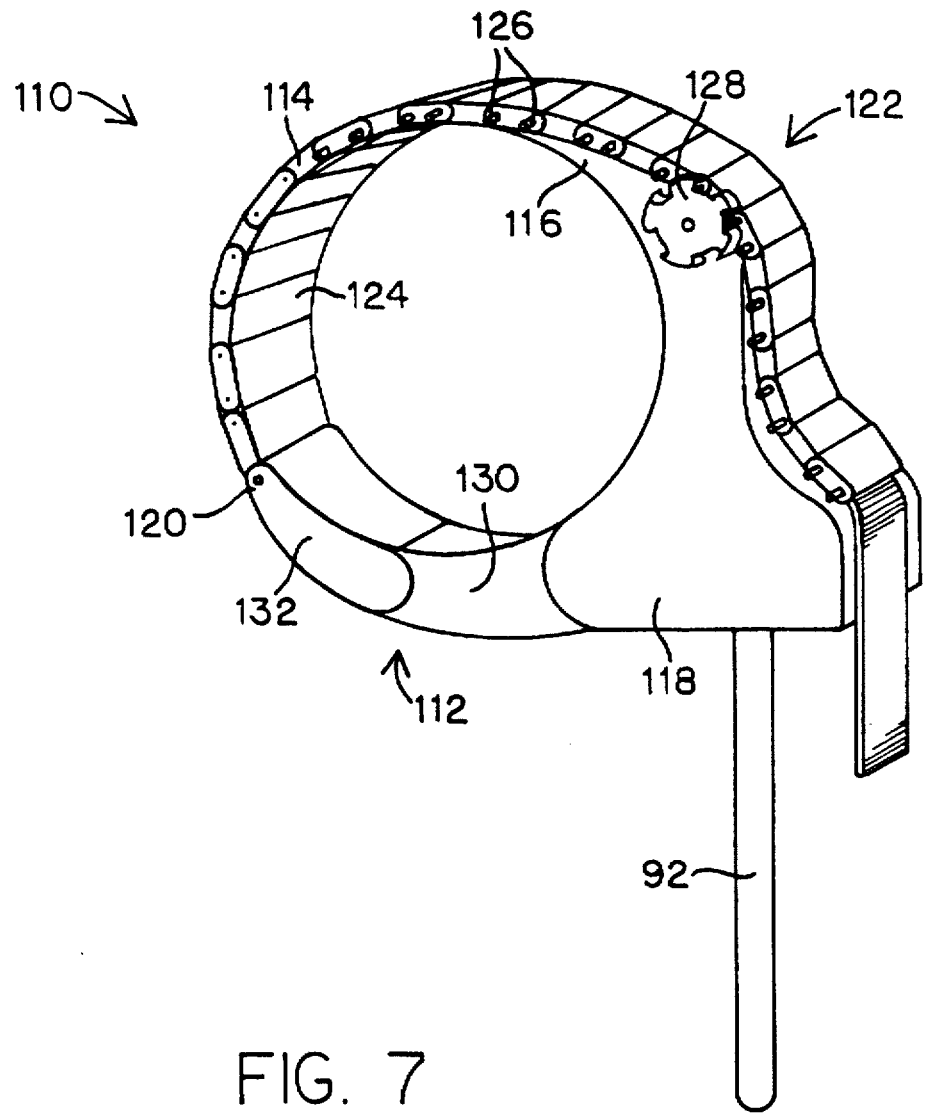
FIG. 7 shows an alternative embodiment of the invention having one articulated arm.
Figure 8:
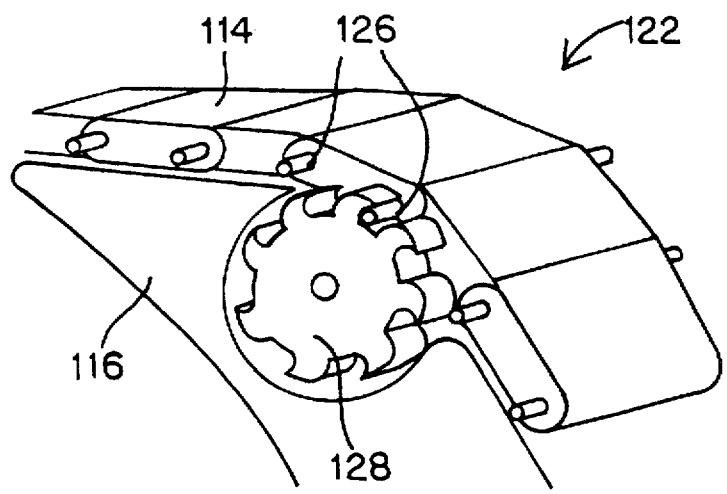
FIG. 8 shows a front end view of the embodiment of FIG. 7.
Figure 9:
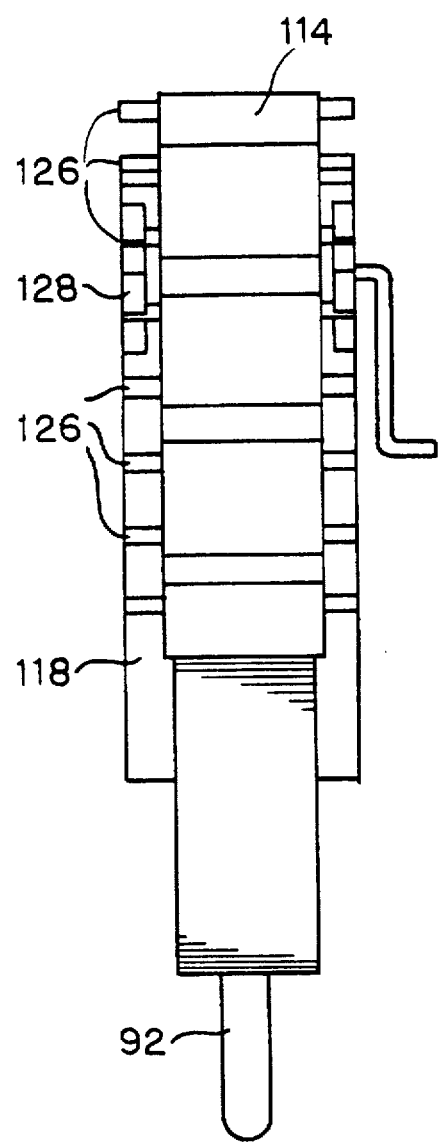
FIG. 9 shows a detail of the chain tightening and locking mechanism of the embodiment of FIG. 7.

Referring to FIGS. 1–9, there are shown two, but not the only embodiments of the invented extremity clamp system. The preferred clamp assembly 10 is shown in use in FIG. 1, holding a thigh in preparation for surgery, and is detailed in FIGS. 2–6. An alternative clamp assembly 110 according to the invention is shown in FIGS. 7–9.

Preferred clamp assembly 10 comprises a base member 12 from which extend two articulated arms 14, 16. A belt 18 extends from the lower arm 14, across the clamp opening, and along the outside top of the upper arm 16, to be secured to the clamp 10 at or near the base member 12. The first end 20 of the belt 18 is preferably connected to the lower arm 14 at or near the base 12, while the second end 28 of the belt 18 passes through a cam system 30 that acts as a tightening and locking means.

Figure 1:
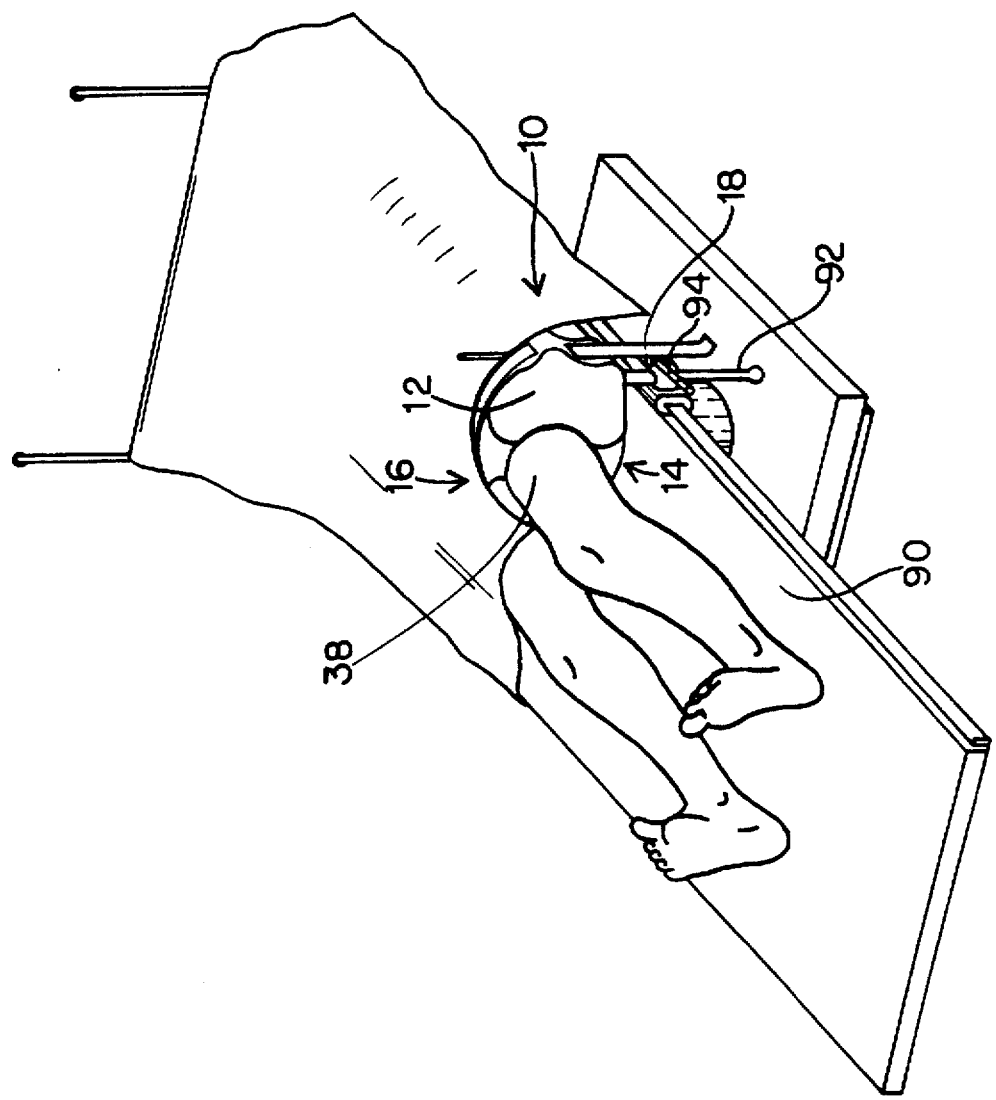
FIG. 1 is an isometric view of one embodiment of the invention, holding a patient's left thigh on an operating table.
Figure 2:
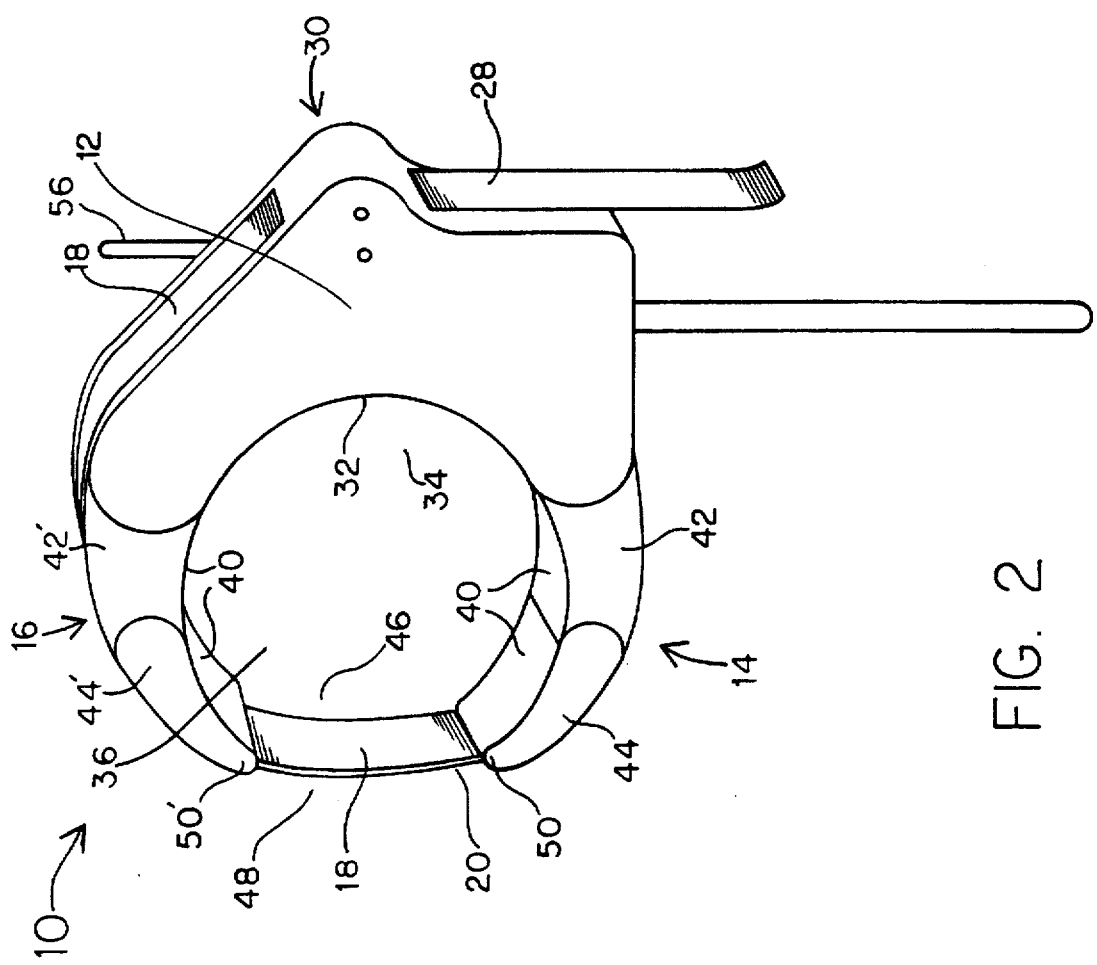
FIG. 2 is an isometric view of the embodiment of FIG. 1, with the clamp assembly in a closed position without a patient's limb.

The base member 12 has a curved inner surface 32 that defines a first side 34 of the clamp interior space 36 for receiving the patient's limb 38. The curved inner surfaces 40, 41 of the arm sections 42, 42', 44, 44' preferably allign with the base inner surface 32 to create a generally circular or cylindrical interior space 36 for the limb 38 when the clamp 10 is in the closed position, as shown in FIGS. 1 and 2. Thus, the articulated arms 14, 16 define the top and bottom of the interior space 36 and may extend to form part or all of the second side 46 of the interior space 36.

In applications for larger limbs, there is typically a gap between the arm distal ends 50, 50' and the belt 18 typically extends across the opening 48 of the clamp 10 between the distal ends 50, 50' to further define the second side 46 of the interior space. For smaller limbs, the articulated arms 14, 16 pivot at their joints to a greater degree to close around the small limb, so that the ends 50, 50' come closer together to touch or nearly touch.

The arm sections 42, 42', 44, 44' are preferably jointed in such a way as to have a large degree of movement relative to each other and to be moved easily and with little resistance. Each section preferably may move about 130°–200° (preferably 180°) around the end of the arm section to which it is attached. Thus, when the clamp 10 is opened, the lower arm 14 may hang down below horizontal, and the upper arm 16 may be lifted up above horizontal, if it is necessary to widen the opening for insertion of a large limb or a limb having a tourniquet cuff or other cushion.

In use, the lower arm 14 is let to hang in the open position, the upper arm 16 is manually raised up, and the limb is inserted into the clamp interior space 36. The limb is held by the user in contact with the base inner surface 32, while the user or an assistant lays the upper arm 16 down on the limb or cuff, and then swings the belt 18 around the outside of the clamp arms, across the top of the upper arm, and inserts the belt through the cam system 30 for fastening. The second end 28 of the belt is pulled by hand to pivot the clamp arms snugly around the limb. The cam system handle 56 is then swung to cause the cam system to grip the belt, tighten the belt typically about another inch to clamp the limb to the desired tightness, and to lock the belt in that desired tightened position. This simple procedure typically produces an optimal and reproducible tightness, however, for special circumstances such as accommodating the particular preferences of a surgeon or a particular surgical procedure, the tightness may be further adjusted by subsequent disengaging/engaging of the cam system 30 while the user simultaneously pulls or loosens the belt by hand.

Figure 3:
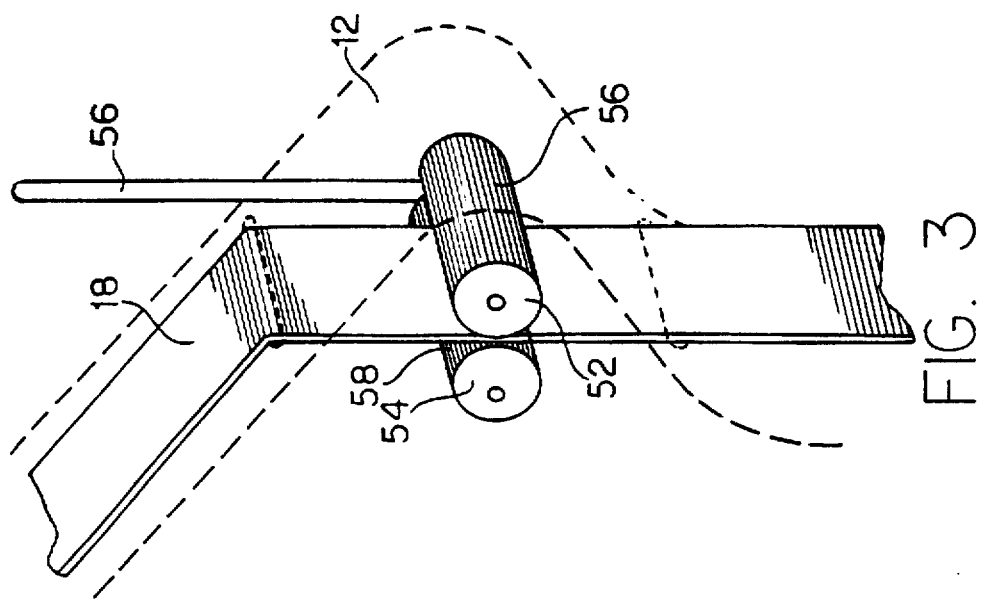
FIG. 3 shows a left side detail of a tightening and locking means of the embodiment of FIG. 1, located in the clamp base member shown in dashed lines.
Figure 4:
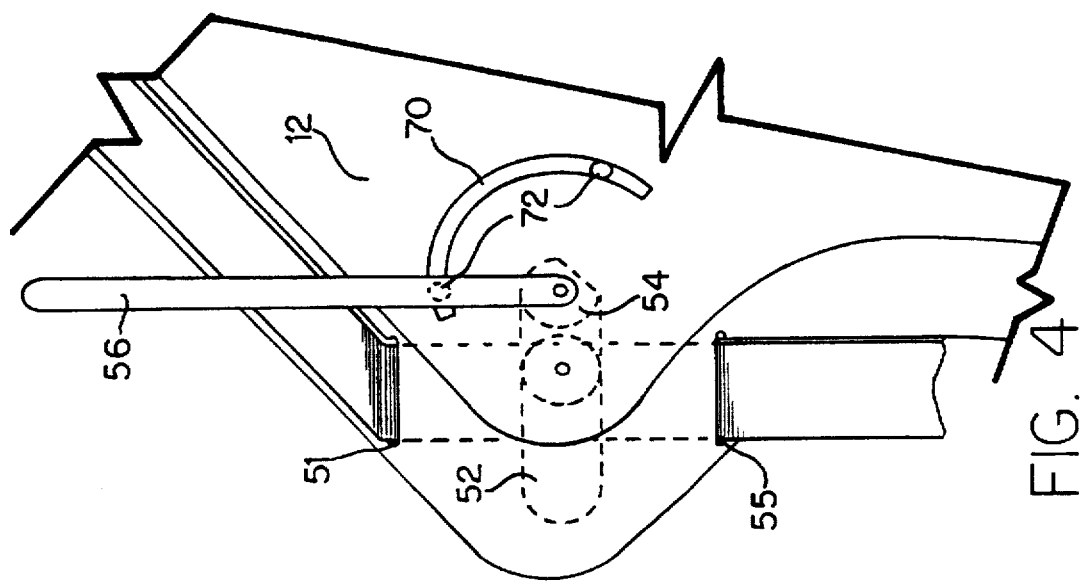
FIG. 4 shows a right side detail of the tightening and locking means of FIG. 3, with the cam system and belt shown in dashed lines inside the base.
Figure 5:
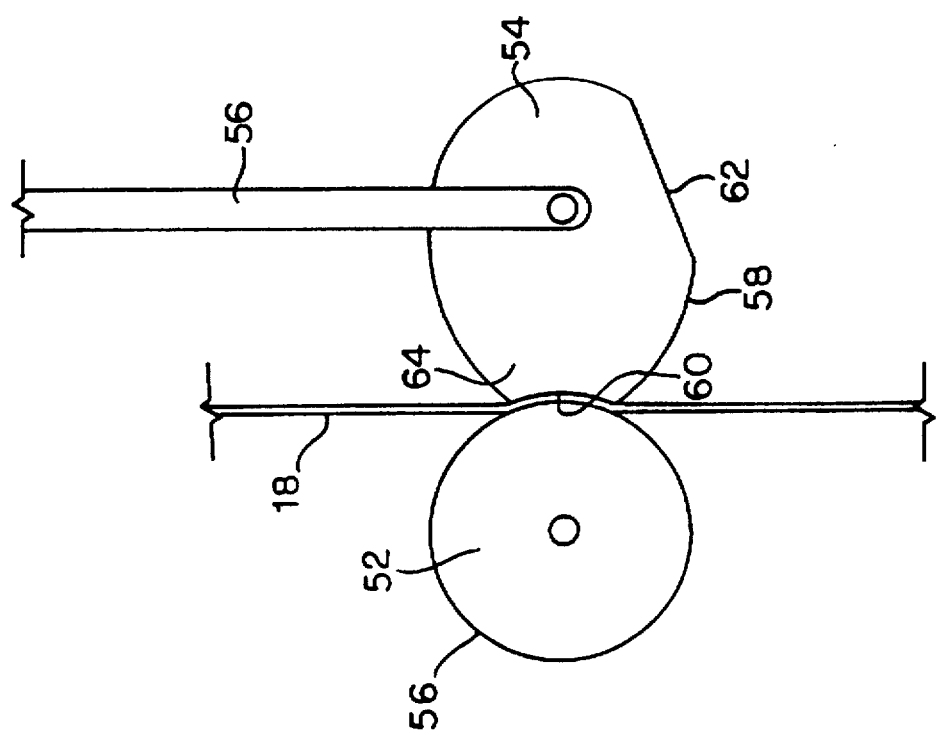
FIG. 5 shows a schematic detail of the cam system of the tightening and locking means of FIG. 3.
Figure 6B:
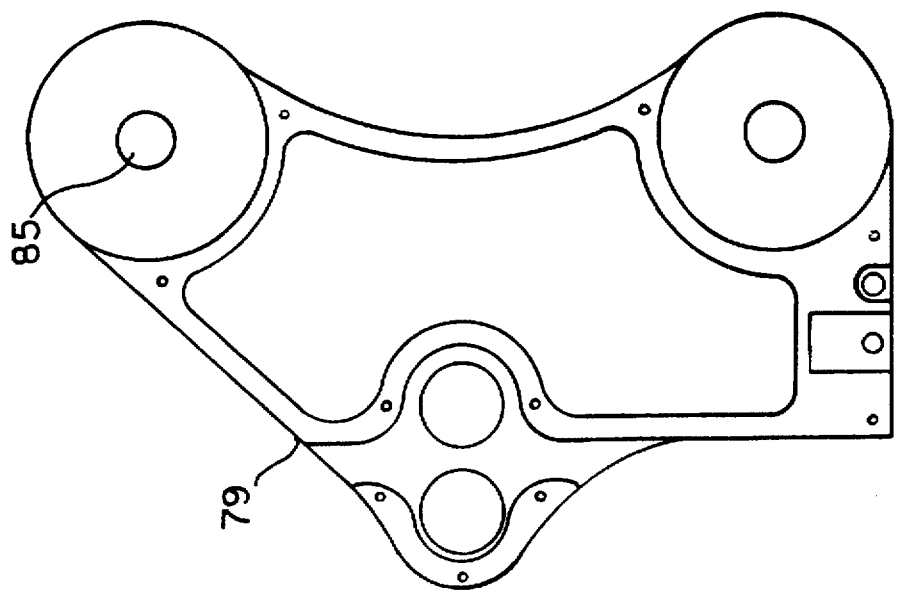
FIGS. 6 A–F show pieces parts of the embodiment of FIG. 1, that is half of a base member and half of two arm sections.
FIGS. 6A and B show left and right sides, respectively, of the left half of a base member.
FIGS. 6C and D show left and right sides, respectively, of the left half of a middle arm section.
FIGS. 6E and F show left and right sides, respectively, of the left half of an end arm section.
Figure 6A:
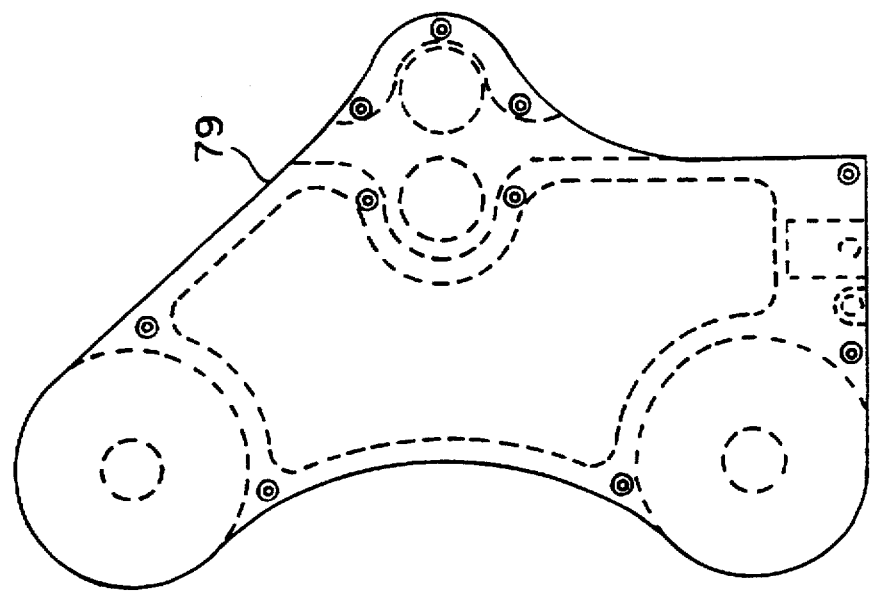
Figure 6D:
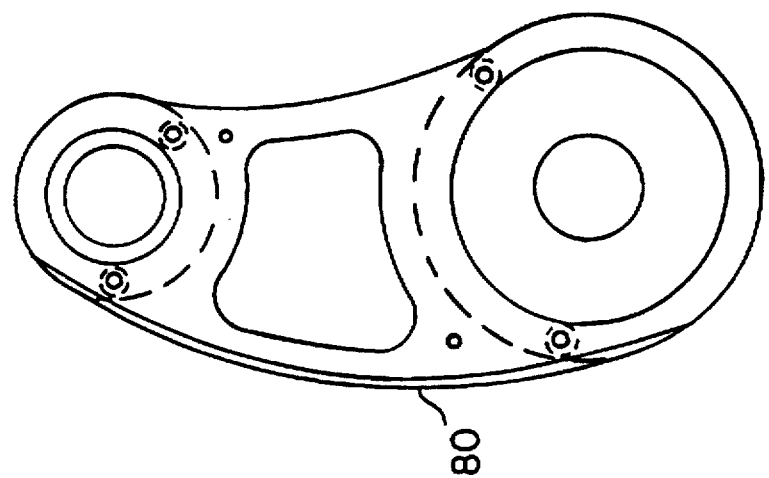
Figure 6C:
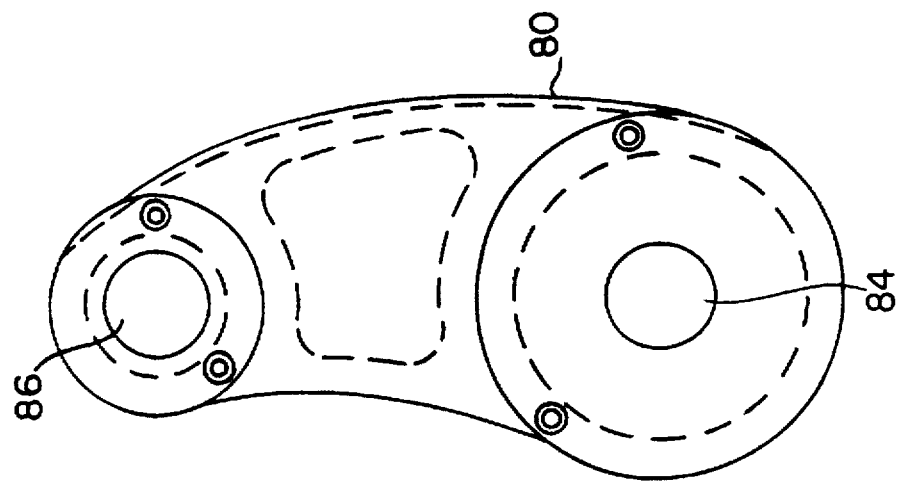
Figure 6F:
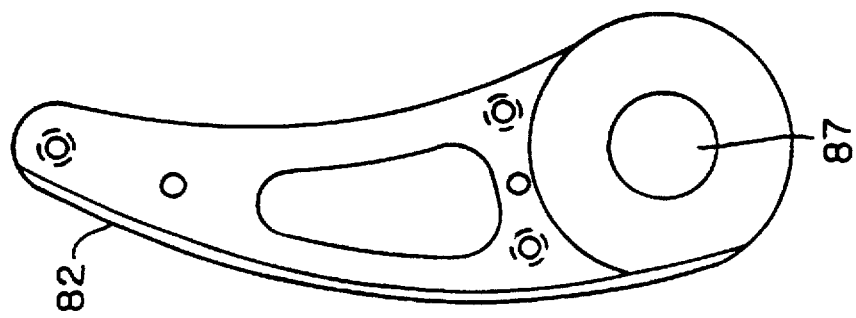
Figure 6E:
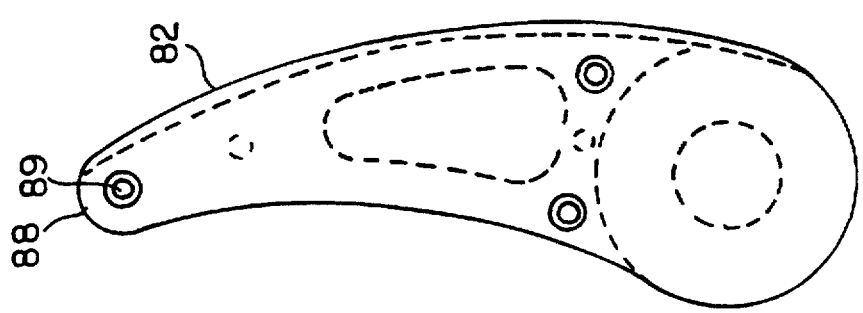

The cam system 30, shown in detail in FIGS. 3–5, is located substantially inside a cavity 53 in the base 12 of the clamp 10. The belt 18 is fed through a slot 51 in the base 12, between a roller 52 and a cam 54 (also called "cam roller"), and out through a lower second slot 55. Both the roller 52 and cam 54 are rotatably mounted inside the base by conventional means. The roller 52 and cam 54 each have serrated surfaces 56, 58 or other frictional surfaces for gripping the belt 18. The roller preferably is cylindrical, and the cam 54 is an eccentric roller with an elongated portion 64 extending out from the axis of the cam. The cam 54 surface has an inwardly-curved or "radiused" surface 60 at or near the elongated portion 64 and a generally flat surface 62 generally opposed from the elongated portion 64.

The cam handle 56 may be moved between unlocked and locked positions, with the movement from unlocked to locked positions also comprising first a period of movement of the belt by the cam to tighten the belt beyond hand-tightness, and then a final movement or snap into a locked position. When the cam handle 56 is in the unlocked position, the cam 54 is in a position where the flat surface 62 faces the belt 18 and the roller 52, maximizing the distance between the cam and roller to provide a gap for free and easy passage of the belt 18. While the user holds the belt end 28 in a hand-tight position, the handle 56 is then moved into the locked position, which rotates the cam extended portion 64 against the belt 18 to move the belt down about an inch to further tighten the belt around the clamp arms. When the radiused surface 60 pushes against the belt and roller, and then mates with the cylindrical roller 52, the belt is locked in place in between the cam and roller. Thus, the radiused surface and roller mate to form a pinch point to lock the belt and, therefore, to lock the clamp arms in the desired degree of tightness around the patient's limb.

As shown schematically shown in FIG. 4, a handle indexing means may be included in the clamp system 10, to make handle movements certain and accurate. For example, the handle movement may be guided in an arc channel 70 cut into the base 12 surface, and the handle may be guided to stop in two positions, i.e. the unlocked and locked positions, with a ball plunger system 72 that cooperates with the channel 70.

Details of some parts of the clamp 10 are shown in FIGS. 6A–F. These figures show half 79 of a base member 12 (FIGS. 6A and B) and half 80, 82 of two upper arm sections, 42', 44' (FIGS. 6C–F), viewed from the right and left side of each piece. The pieces parts making up the other half of the clamp are generally mirror images of those shown in FIGS. 6A–F. The joint between the halves of the base and the middle section comprises a bore 84 and a post 85 received in the bore 84. The joint between the halves of the middle section and the end section also comprises a bore 86 and a post 87 received in the bore 86. The distal end 88 has an belt attachment bore 89 for a fastener for the first end of the belt 18. The arm 16 may be made by connecting mirror image halves together. The lower arm 12 may be made similarly. Examples of dimensions in inches are shown on FIGS. 6 A–F, but these dimensions are not intended to limit the invention to particular dimensions or joint designs. Other joint designs, within the skill of technicians and engineers in the art, may be used. Optionally, the joints of the lower arm 14 may be designed so that, when the clamp is in the open position, the lower arm extends horizontally or slightly above horizontal to support the limb while the clamp is being closed around the limb.

The clamp 10 is preferably connected above an operating or examination table 90, or other platform, by a rigid connection means such as a rod 92 and a universal table clamp 94. One rod 92 slides in and is secured in the table clamp 94. The table clamp 94 typically fastens to the edge of the table 90 and includes a handle for loosening the grip on the rod 92 for raising or lowering the rod 92 and clamp 10.

Preferred materials for the clamp assembly 10 include machined or molded Delrin™ or ABS plastic, aluminum, or other light-weight material. The rod 92 may be stainless steel received in a stainless steel-lined bore in the base 12.

An alternative embodiment, as shown in FIGS. 7–9, is a clamp assembly 110 with a single articulated arm 112 and a flexible band 114 locked to a top extension 116 of the base 118. The band 114 extends from the distal end 120 of the articulated arm 112 and wraps around the limb to engaged a gear wheel system 122. The band 114 has a generally smooth, broad inner surface 124 and protruding pins 126 for being received and pulled forward by the teeth of the wheel 128. Thus, the band 114 lies external to the clamp 110. In use, clamp 110 performs much like clamp 10, with the thigh contacting the upper surface of the articulated arm 112 and wrapped by the locked band 114.

In both clamp designs, arm 112 and arms 14 and 16, provide support for the thigh and preserve a generally circular interior space for the leg. Preferably, each articulated arm has two joints, with one joint being between the base and middle arm sections (42, 42', 130), and another joint between the middle arm sections and the end arm sections (44, 44', 132). Preferably, the arm sections are rigid and greater than about 2 inches in length (preferably 3–6 inches), to provide superior support, when the clamp is closed around the limb, compared to a flexible belt or band. Optionally, an articulated arm may extend further than about half way around the limb, for example, in designs where one long articulated arm with a plurality of joints is used with a short strap means or other connection means for connecting the arm to the base after it wraps around the limb.

In this description and the claims, the term "limb" is intended to include applications where the limb is wrapped or covered with a cuff, cloth, tourniquet or other covering.

Although this invention has been described above with reference to particular means, materials and embodiments, it is to be understood that the invention is not limited to these disclosed particulars, but extends instead to all equivalents within the scope of the following claims.

I claim:

1. A limb clamp assembly for use during examination or surgery, the clamp assembly comprising:

a base member for connection to a platform;

an articulated arm extending generally horizontally from said base member, the arm having a joint, an upper surface for contacting a patient's limb, and a distal end;

a strap means having a first and second end and connected near the first end to the clamp assembly near the articulated arm, for extending from near the said articulated arm distal end around the patient's limb to the base member; and a fastening means for securing the strap means near its second end to the base member for holding the limb against the articulated arm and base member.

2. A limb clamp assembly as in claim 1, wherein the fastening means further comprises a tightening means for pulling the strap means to a tightened position around the limb and a locking means for locking the strap means in the tightened position.

3. A limb clamp assembly as in claim 1, wherein the fastening means comprises a roller and means for rotating the roller against the strap means to tighten the strap means around the patient's limb.

4. A limb clamp assembly as in claim 1, wherein the fastening means comprises a cam roller and means for rotating the cam roller against the strap means to tighten the strap means around the patient's limb.

5. A limb clamp assembly as in claim 4, wherein the fastening means further comprises a cylindrical roller and wherein the strap means is received between the cam roller and the cylindrical roller.

6. A limb clamp assembly as in claim 5, wherein the cam roller comprises an inwardly curved surface for mating with the cylindrical roller to lock the strap means in a tightened position between the cam roller and the cylindrical roller.

7. A limb clamp assembly as set forth in claim 6, wherein the articulated arm has a plurality of joints.

8. A limb clamp assembly as in claim 1, wherein the fastening means comprises a rotatable gear wheel for engaging and moving the strap means to a tightened position.

9. A limb clamp assembly as in claim 1, wherein the articulated arm has a plurality of joints.

10. A limb clamp assembly as in claim 1, further comprising a second articulated arm extending from said base member, the second articulated arm having a joint and a lower surface for contacting the patient's limb.

11. A limb clamp assembly as set forth in claim 1, wherein the articulated arm comprises first and second arm sections being connected by said joint, and wherein the first arm section moves between 130°–200° around the second arm section.

12. A limb clamp assembly for use during examination or surgery, the clamp assembly comprising:

a base member for connection to a platform;

spaced upper and lower articulated arms extending generally horizontally from said base member and defining a clamp interior space between them, each arm having a joint, an inner surface for contacting a patient's limb, and a distal end;

a strap means having a first and second end and connected near its first end to the clamp assembly near one of the articulated arms, for extending outside the articulated arms and around the patient's limb to near the base member; and a fastening means for securing the strap means near its second end to the base for holding the limb inside said interior space.

13. A limb clamp assembly as in claim 12, wherein the fastening means further comprises a tightening means for pulling the strap means to a tightened position around the limb and a locking means for locking the strap means in the tightened position.

14. A limb clamp assembly as in claim 12, wherein the fastening means comprises a roller and means for rotating the roller against the strap means to tighten the strap means around the patient's limb.

15. A limb clamp assembly as set forth in claim 14, wherein each articulated arm has a plurality of joints.

16. A limb clamp assembly as in claim 12, wherein the fastening means comprises a cam roller and means for rotating the cam roller against the strap means to tighten the strap means around the patient's limb.

17. A limb clamp assembly as in claim 16, wherein the fastening means further comprises a cylindrical roller and wherein the strap means is received between the cam roller and the cylindrical roller.

18. A limb clamp assembly as in claim 17, wherein the cam roller comprises an inwardly curved surface for mating with the cylindrical roller to lock the strap means in a tightened position between the cam roller and the cylindrical roller.

19. A limb clamp assembly as set forth in claim 17, wherein each articulated arm has a plurality of joints.

20. A limb clamp assembly as in claim 12, wherein each articulated arm has a plurality of joints.

* * * * *